United States Patent

Blanc et al.

[11] Patent Number: 5,155,095
[45] Date of Patent: Oct. 13, 1992

[54] FRAGRANCE INGREDIENT

[75] Inventors: Pierre-Alain Blanc, Crassier; Roland Aschiero, Bernex, both of Switzerland

[73] Assignee: Firmenich S.A., Geneva, Switzerland

[21] Appl. No.: 810,660

[22] Filed: Dec. 19, 1991

[30] Foreign Application Priority Data

Feb. 27, 1991 [CH] Switzerland .................. 599/91
Oct. 25, 1991 [CH] Switzerland .................. 3138/91

[51] Int. Cl.$^5$ ............................................. A61K 7/46
[52] U.S. Cl. ............................ 512/21; 560/35; 560/45

[58] Field of Search ............... 512/21; 560/35, 45

[56] References Cited

U.S. PATENT DOCUMENTS 4,806,363  2/1989  Mookherjee et al. .......... 512/21

Primary Examiner—James H. Reamer
Attorney, Agent, or Firm—Pennie & Edmonds

[57] ABSTRACT

The reaction product of methyl anthranilate with 3-phenylbutanal is useful as a perfuming ingredient for the preparation of perfuming compositions and perfumed articles, to which it imparts a floral-green odor note of the yellow flower type.

11 Claims, No Drawings

FRAGRANCE INGREDIENT

BRIEF SUMMARY OF THE INVENTION

The invention relates to a composition of matter consisting of the product obtained by reacting methyl anthranilate with 3-phenylbutanal.

The invention further relates to a method to confer, improve, enhance or modify the odor properties of a perfuming composition or a perfumed article, which method comprises adding to said composition or article the above-mentioned composition of matter.

The invention further provides a perfuming composition or a perfumed article containing as an active ingredient the above-mentioned composition of matter.

BACKGROUND OF THE INVENTION

The present invention relates to the perfume industry and, in particular, it concerns a novel perfuming ingredient which belongs to the group of compounds generally known as Schiff bases.

The Schiff bases are well-known in perfumery. Thus, the reference book by S. Arctander, Perfume and Flavor chemicals, Montclair, N.J., USA (1969), cites a great number of such bases [see for example sections 26, 157, 244, 624, 655, 665, 755, 759, 836, 1549, 1621, 1753, 1782, 1799, 1955, 2080, 2125, 2280 or 3070]. The odor characters of these Schiff bases are often similar. Thus, a great majority of these products are said to possess floral, fruity odors, namely of the citrus type and, more particularly, reminiscent of the odor of the orange-flower.

Other Schiff bases have been described more recently in U.S. Pat. Nos. 4,775,720, 4,839,083 and 4,840,801, as well as in JP 62-153212. However, in spite of the number of products of this type described to this day, we have not found any mention of the composition of matter according to the invention in the prior art.

THE INVENTION

The present invention provides a novel product of the type mentioned above, i.e. the composition of matter consisting of the product obtained by reacting methyl anthranilate with TRIFERNAL® (3-phenylbutanal; origin: Firmenich SA, Geneva, Switzerland).

We have now discovered that this composition of matter possesses very original odor properties, wholly surprising in view of the prior art. It develops, in fact, an odor of the floral-yellow flower type, with a green character which is more pronounced in the head note than in the bottom note.

This is a very natural odor note, reminiscent of the odor of the alpine flora in the spring, and which is very original relative to the odor notes of the prior known Schiff bases. This is clearly seen in the table presented hereinafter, which describes the results of the comparative olfactive evaluation, carried out by a panel of expert perfumers, between the composition of matter which is the object of the present invention and several Schiff bases chosen amongst those more currently used in perfumery.

TABLE

| Product | Descriptive source/origin | Orange flower | Neroli | Petit-grain | Green | White flower | Pow-dery | Yellow flower | Others |
|---|---|---|---|---|---|---|---|---|---|
| 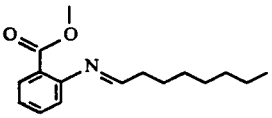 | Firmenich SA | +++ | ++ | + | + | | | | Aldehydic |
| 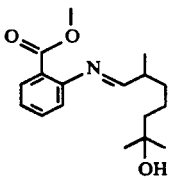 | Arctander 1735 | +++ | ++ | | | ++ | | | Lily of the valley |
| 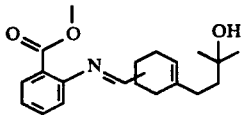 | Arctander 2080 | ++ | ++ | | | ++ | | | |
| 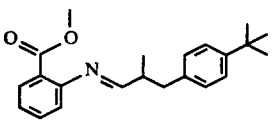 | Arctander 1799 | + | | | ++ | | ++ | | Cyclamen/ aqueous |
| 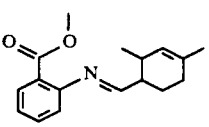 | Firmenich SA | + | | ++ | +++ | | | | |

TABLE-continued

| Product | Descriptive source/origin | Orange flower | Neroli | Petit-grain | Green | White flower | Pow-dery | Yellow flower | Others |
|---|---|---|---|---|---|---|---|---|---|
| 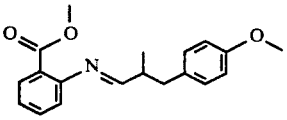 | U.S. Pat. No. 4,840,801 JP 62-153212 | | + | | | | +++ | | Anisic/cassie |
| 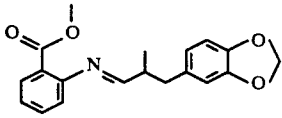 | U.S. Pat. No. 4,839,083 JP 62-153212 | ++ | | | | ++ | ++ | | |
| Composition of matter according to the present invention | See examples | | | | ++ | | + | +++ | Mimosa |

Order of decreasing intensity +++ → ++ → +

This table shows that, unlike what is observed with the known Schiff bases cited, the composition of matter according to the present invention does not possess any floral, citrus type, odor character, and that its odor is totally devoid of the orange-flower note which is so common amongst the other Schiff bases. Furthermore, its dominant note, i.e. the yellow flower type character, is very surprising since none of the other Schiff bases possesses this odor character.

In fact, we have not found in the prior art any Schiff base possessing the combination of odor properties which is characteristic of the composition of matter according to the invention. The floral note of the latter is distinctly more pronounced than that of the prior known Schiff bases, whose odors are characterized rather by floral-fruity notes. On the other hand, the original dominant yellow flower type character of the composition of the invention is particularly useful. In fact, although its odor is reminiscent of that of its parent aldehyde 3-phenylbutanal, it possesses a softer character, which renders the composition of matter according the invention easier to use in perfumery than said aldehyde.

As a result, of its odor properties, the composition of matter according to the invention can be used with equal advantage in both fine and technical perfumery. It can be employed for the preparation of perfuming compositions and perfumed articles of varied nature. Thus, it is very convenient for preparing perfumes and colognes, or for perfuming soaps, shower or bath gels, shampoos, cosmetic preparations or body or air deodorizers.

As can be appreciated from the examples presented further on, the excellent substantivity of its odor note renders the use of the composition of matter according to the invention quite advantageous for perfuming detergents and fabric softeners, while it is also convenient for perfuming household products.

For these applications, the composition of matter according to the invention may be used alone or, as it is more current in perfumery, in admixture with other perfuming ingredients, solvents or adjuvants of current use in perfumery. Examples of the latter can be found in the reference books in the art such as S. Arctander's book previously cited.

The concentrations in which the composition of matter according to the invention can be used vary in a wide range of values. It is quite well-known known that such values depend on the desired perfuming effect and are a function of the nature of the article one wishes to perfume. By way of example, concentrations of the order of 1 to 10% by weight, or even more, of composition of matter, relative to the weight of the perfuming composition into which it is incorporated, can be cited. Much lower concentrations can however be used, namely when said composition of matter is employed for perfuming the above-cited varied articles.

The reaction product of methyl anthranilate with TRIFERNAL® can be prepared according to the usual methods for synthesizing Schiff bases, by reacting the two starting products. It is a well-known fact that, depending on the nature of said starting compounds, their reaction product may consist of a mixture of conjugation and/or configuration isomers.

In the present case, it has been observed that the nature of the composition of matter consisting of the reaction product obtained was also dependent on the reaction conditions, examples of which are given hereinafter, and, in particular, on the temperature. Thus, the reaction product could contain variable quantities of the compounds of formula

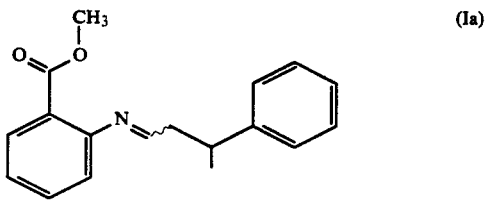

(Ia)

or

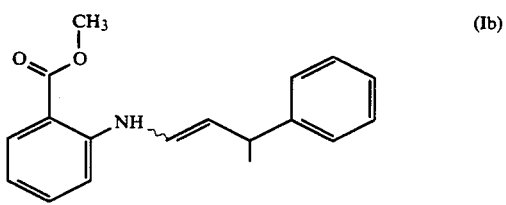

(Ib)

wherein the wavy line stands for a cis or trans conformation bond, or of formula

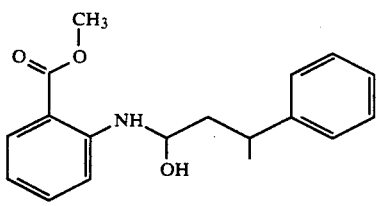

(Ic)

From an olfactive point of view, all these mixtures possessed similar properties and could thus be used in perfumery in an interchangeable manner, to produce comparable odor effects. If desired, the individual components could be separated by way of the usual techniques and their individual analytical data are presented further on.

The following preparation examples, wherein the temperatures are indicated in degrees centigrade and the abbreviations have the usual meaning in the art, describe the compositions of matter according to the invention obtained following different preparation methods.

METHOD 1

A three-neck flask, equipped with a magnetic stirrer and a water separator, was charged with 90.6 g (0.60 mol) of methyl anthranilate, 74.0 g (0.50 mol) of 3-phenylbutanal and 300 ml of toluene. The mixture was brought to reflux for 20 h, until an amount of water corresponding to 100% yield (9.0 ml) had been formed. The separator was then replaced by a very short column head and the toluene was distilled at atmospheric pressure. After cooling down, a vacuum of $15 \times 10^2$ Pa was gradually applied and the excess of methyl anthranilate distilled (max. temp. of the oil bath: 110°). The mixture was cooled down, placed under vacuum and the reaction product was distilled (bath temp.: 110°/0.1 Pa) rather quickly, while the temperature was carefully controlled to avoid decomposition.

FIG. 1 shows the proton NMR spectrum, taken at 360 MHz in CHCl$_3$, of the reaction product obtained.

The GC/MS coupling spectra (capillary column SPB1 30 m, 160°-230°, 7 min) of the components of the mixture were the following:

A. Methyl N-(3-phenylbutylidene)anthranilate (10% by weight of the mixture)
MS: 281(M+,20), 266(6), 234(43), 131(51), 117(55), 105(100), 77(98)

B. Methyl (E)-N-(3-phenyl-1-butenyl)anthranilate (30% by weight of the mixture)
MS: 281(M+,37), 266(59), 234(73), 117(100), 105(78), 77(85)

C. Methyl (Z)-N-(3-phenyl-1-butenyl)anthranilate (60% of the weight of the mixture)
MS:281(M+,42) 266(71), 234(84), 116(80), 105(84), 77(100)

METHOD 2

A three-neck flask, equipped with a magnetic stirrer and a water separator, was charged, at 20° and under vigorous stirring, with 90.6 g (0.60 mol) of methyl anthranilate to which were added 5 g of a total of 74 g (0.50 mol) of 3-phenylbutanal. The reaction was exothermic and the temperature increased to 25°. After heating to 45°, the remaining aldehyde was introduced in 1 h. At this same temperature a vacuum of 10 mm ($13 \times 10^2$ Pa) was applied gradually and then the mixture was heated for 2 h at 60° to eliminate, by distillation, part of the water (4.85 g) formed during the reaction. The unreacted starting products were distilled (bath temp.: 110°/0.1 Pa) in the same way.

The proton NMR spectrum, obtained at 360 MHz in CDCl$_3$, executed on the residue (around 140 g) previously obtained is represented in FIG. 2. It confirms the presence in the mixture of the three compounds A (10% by weight), B (30% by weight) and C (35% by weight) already identified in the product obtained according to method 1 and it shows that the mixture also contained 25% by weight of methyl N-(1-hydroxy-3-phenylbutyl-)anthranilate (D).

METHOD 3

A 3 l reactor equipped with a stirrer, a 10 cm Vigreux column, a distillation bridge and a fraction separator, was charged with 815.4 g (5.4 mol) of methyl anthranilate, to which there were added, in 1 h30, 666.0 g (4.5 mol) of 3-phenylbutanal. The temperature of the reactor increased from 20° to 47°-50°. Stirring was continued and the temperature of the reaction mixture was slowly increased to 65°. The pressure was then reduced and, still under stirring, the heating temperature was increased to 90°-95° in 6 h, while the pressure was gradually increased to $10^2$ Pa. 90 G of distillate were collected and the desired product was obtained as residue (1385 g; yield: 93.5%).

The NMR analysis of this product showed that it consisted of a mixture containing about 69% by weight of D (see method 2), 10% by weight of B, 10% by weight of C and 4% by weight of A. It also contained 7% by weight of the starting aldehyde.

The NMR analytical data of the individual components of these mixtures were the following:

A. Methyl N-(3-phenylbutylidene)anthranilate

NMR($^1$H,360 MHz,CDCl$_3$): 1.34(d,J~7 Hz,3H); 2.78(m,2H); 3.25(d×q, J~7, 7 Hz, 1H); 7.58(J~5 Hz,1H) δ ppm B. Methyl (E)-N-(3-phenyl-1-butenyl)anthranilate NMR($^1$H,360 MHz,CDCl$_3$): 1.41(d,J~7 Hz,3H); 3.53(quint,J~7 Hz,1H); 3.83(s,3H); 5.34(dd,J~13, 7 Hz,1H); 6.50(dd,J~13, 10 Hz,1H); 6.63-7.83(several m,9H); 9.57(broad d,J~10 Hz,1H) δ ppm
NMR($^{13}$C,CDCl$_3$): 22.4(q); 40.3(d); 51.7(s); 115.6(d); 124.6(d) δ ppm C. Methyl (Z)-N-(3-phenyl-1-butenyl)anthranilate NMR($^1$H,360 MHz,CDCl$_3$): 1.44(d,J~7 Hz,3H); 3.86(m, part. covered, 1H); 3.86(s,3H); 4.81(t,J=9 Hz,1H); 6.47(dd,J~11, 9 Hz,1H); 6.63-7.83(several m,9H); 9.81(broad d,J~11 Hz,1H) δ ppm
NMR($^{13}$C,CDCl$_3$): 22.5(q); 36.6(d); 51.7(q); 113.8(d); 122.6(d) δ ppm D. Methyl N-(1-hydroxy-3-phenylbutyl)anthranilate NMR($^1$H,360 MHz,CDCl$_3$): 1.35(d,J=7 Hz,3H); 2.06-2.24(m,2H); 3.05(m,1H); 3.80(s,3H); 4.71(m,1H); 6.20(d,J~8 Hz,1H); 6.42(d, J~8 Hz,1H): 6.54-8.00(several m,7H); 7.84(m,part. covered, 1H); 8.11(d,J~6 Hz,1H) δ ppm
NMR($^{13}$C,CDCl$_3$): 22.4(q); 36.7(d); 44.8(t); 51.5(q); 61.4(d) δ ppm The invention will now be described in a more detailed manner by way of the following examples.

EXAMPLE 1

Preparation of a perfuming composition

A base perfuming composition was prepared by admixing the following ingredients:

| Ingredients | Parts by Weight |
| --- | --- |
| Hexylcinnamic aldehyde | 2000 |
| Benzyl salicylate | 2000 |
| Linalol | 1000 |
| Citronellol | 1000 |
| 10%* Amyl allyl glycolate | 500 |
| Allyl cyclohexylpropanate | 100 |
| α-Ionone | 100 |
| Synth. cassis oil | 200 |
| Synth. jasmin oil | 500 |
| 2,4-Dimethyl-3-cyclohexene-1-carbaldehyde | 300 |
| EXALTEX ®[1)] | 800 |
| FLOROL ®[2)] | 500 |
| Total | 9500 |

*in dipropyleneglycol
[1)]mixture containing cyclopentadecanolide; origin: Firmenich SA, Geneva, Switzerland
[2)]tetrahydro-2-isobutyl-4-methyl-4(2H)-pyranol; origin: Firmenich SA, Geneva, Switzerland To this base composition of the floral-green type there were added 250 parts by weight of the composition of matter according to the invention. A novel perfuming composition was thus obtained which possessed an odor note having a distinct floral character, reminiscent of the odor of the yellow flowers (buttercup kind). This composition exhaled an entirely different odor from that obtained upon use, in the same conditions, of the prior known Schiff bases, the odor character of the novel composition being totally oriented towards a very natural floral note and not at all in the direction of the orange-flower odor.

EXAMPLE 2

Substantivity Test

A batch of textiles was treated, during its washing cycle, with a fabric softener to which 0.1% by weight of the composition of matter according to the invention had been added. After this treatment, the wet textiles exhaled an odor which was characterized by a pleasant note of the yellow flower type. As for the dry textiles, they still developed a strong floral-green odor, whose green note was reminiscent of the odor character of 3-phenylbutanal. The thus observed substantivity of the composition of matter according to the invention is all the more surprising and interesting since the above-mentioned starting aldehyde is not substantive at all.

What is claimed is:

1. A composition of matter consisting of the product obtained by reacting methyl anthranilate with 3-phenylbutanal.

2. The composition of matter according to claim 1, containing at least one compound of formula

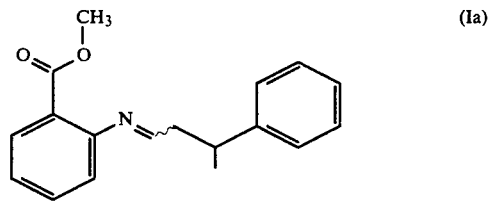

or

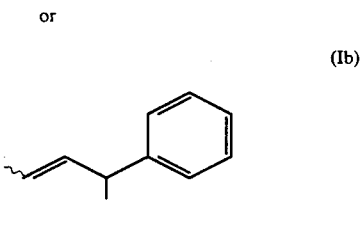

wherein the wavy line stands for a cis or trans conformation bond, or of formula

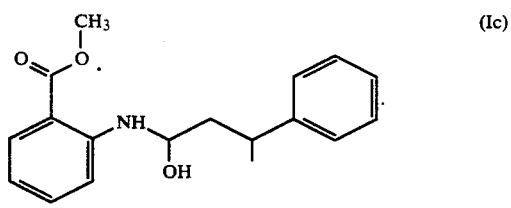

3. A method to confer, improve, enhance or modify the odor properties of a perfuming composition or a perfumed article, which method comprises adding to said composition or article a composition of matter according to claim 1 or 2.

4. A perfuming composition containing as an active ingredient a composition of matter according to claim 1 or 2.

5. A perfumed article containing as an active ingredient a composition of matter according to claim 1 or 2.

6. An article according to claim 5, in the form of a perfume or cologne, a soap, a shower or bath gel, a shampoo, a cosmetic preparation, a body or air deodorant, a detergent or a fabric softener, or a household product.

7. A perfuming composition according to claim 4, having a floral odor, of the yellow flower type.

8. A perfumed article according to claim 5, having a floral odor, of the yellow flower type.

9. Methyl N-(3-phenyl-1-butenyl)anthranilate.

10. Methyl N-(3-phenylbutylidene)anthranilate.

11. Methyl N-(1-hydroxy-3-phenylbutyl)anthranilate.

* * * * *

UNITED STATES PATENT AND TRADEMARK OFFICE
CERTIFICATE OF CORRECTION

PATENT NO. : 5,155,095

DATED : October 13, 1992

INVENTOR(S) : Pierre-Alain Blanc; Roland Aschiero

It is certified that error appears in the above-indentified patent and that said Letters Patent is hereby corrected as shown below:

On the title page, Item [56] Reference Cited

Under "References Cited" U.S. PATENT DOCUMENTS, please add the following references:

| | | | |
|---|---|---|---|
| 4,978,653 | 12/90 | Koshino et al. | 512/21 |
| 4,824,828 | 4/89 | Mookherjee et al. | 512/21 |
| 5,008,437 | 4/91 | Mookherjee et al. | 560/35 |

Signed and Sealed this

Fifth Day of October, 1993

Attest:

BRUCE LEHMAN

Attesting Officer     Commissioner of Patents and Trademarks